United States Patent
Rudnic et al.

(10) Patent No.: US 7,108,859 B2
(45) Date of Patent: Sep. 19, 2006

(54) ANTINEOPLASTIC PRODUCT, USE AND FORMULATION THEREOF

(75) Inventors: Edward M. Rudnic, N. Potomac, MD (US); James D. Isbister, Potomac, MD (US); Donald J. Treacy, Jr., Annapolis, MD (US); Sandra E. Wassink, Frederick, MD (US)

(73) Assignee: Advancis Pharmaceutical Corporation, Germantown, MD (US)

( * ) Notice: Subject to any disclaimer, the term of this patent is extended or adjusted under 35 U.S.C. 154(b) by 0 days.

(21) Appl. No.: 10/274,931

(22) Filed: Oct. 21, 2002

(65) Prior Publication Data

US 2003/0104058 A1   Jun. 5, 2003

Related U.S. Application Data

(63) Continuation of application No. 09/791,905, filed on Feb. 22, 2001, now abandoned, which is a continuation-in-part of application No. 09/687,235, filed on Oct. 13, 2000, now abandoned.

(51) Int. Cl.
  *A61K 9/00*   (2006.01)
  *A61K 9/48*   (2006.01)
  *A61K 9/20*   (2006.01)
  *A61K 9/22*   (2006.01)
  *A61K 9/14*   (2006.01)

(52) U.S. Cl. ............... 424/400; 424/451; 424/464; 424/468; 424/489; 424/502

(58) Field of Classification Search ........... 424/422, 424/430, 436, 443, 427, 437, 464, 465, 468, 424/480, 400, 451, 489, 502
See application file for complete search history.

(56) References Cited

U.S. PATENT DOCUMENTS 4,904,476 A * 2/1990 Mehta et al.
5,472,708 A * 12/1995 Chen
5,719,132 A * 2/1998 Lin et al.

* cited by examiner

*Primary Examiner*—Humera N. Sheikh
(74) *Attorney, Agent, or Firm*—Elliot M. Olstein; Raymond E. Stauffer

(57) ABSTRACT

An antineoplastic product is comprised of at least three dosages forms, each of which has a different release profile, with the $C_{max}$ for the antineoplastic product being reached in less than about twelve hours. In one embodiment, there is an immediate release dosage form, as well as two or more delayed release dosage forms, with each of the dosage forms having a different release profile, wherein each reaches a $C_{max}$ at different times.

41 Claims, No Drawings

ANTINEOPLASTIC PRODUCT, USE AND FORMULATION THEREOF

This application is a continuation of U.S. application Ser. No. 09/791,905, filed on Feb. 22, 2001 now abandoned, which is a continuation-in-part of U.S. application Ser. No. 09/687,235, filed on Oct. 13, 2000 now abandoned.

This invention relates to an antineoplastic product, as well as to the use and formulation thereof.

A wide variety of antineoplastics have been used, and will be used, in order to combat cancer. In general, such antineoplastics can be administered by a repeated dosing of immediate release dosage forms, which results in poor compliance or as a controlled release formulation (slow release) at higher administered doses. The present invention is directed to providing for an improved antineoplastic product.

In accordance with one aspect of the present invention, there is provided an antineoplastic pharmaceutical product which is comprised of at least two, preferably at least three, antineoplastic dosage forms. Such dosage forms are formulated so that each of the dosage forms has a different release profile.

In a particularly preferred embodiment, there are at least two, preferably at least three dosage forms, each of which has a different release profile and the release profile of each of the dosage forms is such that the dosage forms each start release of the antineoplastic contained therein at different times after administration of the antineoplastic product.

Thus, in accordance with an aspect of the present invention, there is provided a single or unitary antineoplastic product that has contained therein at least two, preferably at least three antineoplastic dosage forms, each of which has a different release profile, whereby the antineoplastic contained in each of such dosage forms is released at different times.

In accordance with a further aspect of the invention, the antineoplastic product may be comprised of at least four different dosage forms, each of which starts to release the antineoplastic contained therein at different times after administration of the antineoplastic product.

The antineoplastic product generally does not include more than five dosage forms with different release times.

In accordance with a preferred embodiment, the antineoplastic product has an overall release profile such that when administered the maximum serum concentration of the total antineoplastic released from the product is reached in less than twelve hours, preferably in less than eleven hours. In an embodiment, the maximum serum concentration of the total antineoplastic released from the antineoplastic product is achieved no earlier than four hours after administration.

In accordance with one preferred embodiment of the invention, there are at least three dosage forms. One of the at least three dosage forms is an immediate release dosage form whereby initiation of release of the antineoplastic therefrom is not substantially delayed after administration of the antineoplastic product. The second and third of the at least three dosage forms is a delayed dosage form (which may be a pH sensitive or a non-pH sensitive delayed dosage form, depending on the type of antineoplastic product), whereby the antineoplastic released therefrom is delayed until after initiation of release of the antineoplastic from the immediate release dosage form. More particularly, the antineoplastic released from the second of the at least two dosage forms achieves a $C_{max}$ (maximum serum concentration in the serum) at a time after the antineoplastic released from the first of the at least three dosage forms achieves a $C_{max}$ in the serum, and the antineoplastic released from the third dosage form achieves a $C_{max}$ in the serum after the $C_{max}$ of antineoplastic released from the second dosage form.

In one embodiment, the second of the at least two dosage forms initiates release of the antineoplastic contained therein at least one hour after the first dosage form, with the initiation of the release therefrom generally occurring no more than six hours after initiation of release of antineoplastic from the first dosage form of the at least three dosage forms.

In general, the immediate release dosage form produces a $C_{max}$ for the antineoplastic released therefrom within from about 0.5 to about 2 hours, with the second dosage form of the at least three dosage forms producing a $C_{max}$ for the antineoplastic released therefrom in no more than about four hours. In general, the $C_{max}$ for such second dosage form is achieved no earlier than two hours after administration of the antineoplastic product; however, it is possible within the scope of the invention to achieve $C_{max}$ in a shorter period of time.

As hereinabove indicated, the antineoplastic product may contain at least three or at least four or more different dosage forms. For example, if the antineoplastic product includes a third dosage form, the antineoplastic released therefrom reaches a $C_{max}$ at a time later than the $C_{max}$ is achieved for the antineoplastic released from each of the first and second dosage forms. In a preferred embodiment, release of antineoplastic from the third dosage form is started after initiation of release of antineoplastic from both the first dosage form and the second dosage form. In one embodiment, $C_{max}$ for antineoplastic release from the third dosage form is achieved within eight hours.

In another embodiment, the antineoplastic product contains at least four dosage forms, with each of the at least four dosage forms having different release profiles, whereby the antineoplastic release from each of the at least four different dosage forms achieves a $C_{max}$ at a different time.

As hereinabove indicated, in a preferred embodiment, irrespective of whether the antineoplastic contains at least two or at least three or at least four different dosage forms each with a different release profile, $C_{max}$ for all the antineoplastic released from the antineoplastic product is achieved in less than twelve hours, and more generally is achieved in less than eleven hours.

In a preferred embodiment, the antineoplastic product is a once a day product, whereby after administration of the antineoplastic product, no further product is administered during the day; i.e., the preferred regimen is that the product is administered only once over a twenty-four hour period. Thus, in accordance with the present invention, there is a single administration of an antineoplastic product with the antineoplastic being released in a manner such that overall antineoplastic release is effected with different release profiles in a manner such that the overall $C_{max}$ for the antineoplastic product is reached in less than twelve hours. The term single administration means that the total antineoplastic administered over a twenty-four hour period is administered at the same time, which can be a single tablet or capsule or two or more thereof, provided that they are administered at essentially the same time.

Applicant has found that a single dosage antineoplastic product comprised of at least three antineoplastic dosage forms each having a different release profile is an improvement over a single dosage antineoplastic product comprised of an antineoplastic dosage form having a single release profile. Each of the dosage forms of antineoplastic in a pharmaceutically acceptable carrier may have one or more antineoplastics and each of the dosage forms may have the same antineoplastic or different antineoplastics.

It is to be understood that when it is disclosed herein that a dosage form initiates release after another dosage form, such terminology means that the dosage form is designed and is intended to produce such later initiated release. It is known in the art, however, notwithstanding such design and intent, some "leakage" of antineoplastic may occur. Such "leakage" is not "release" as used herein.

If at least four dosage forms are used, the fourth of the at least four dosage forms may be a sustained release dosage form or a delayed release dosage form. If the fourth dosage form is a sustained release dosage form, even though $C_{max}$ of the fourth dosage form of the at least four dosage forms is reached after the $C_{max}$ of each of the other dosage forms is reached, antineoplastic release from such fourth dosage form may be initiated prior to or after release from the second or third dosage form.

The antineoplastic product of the present invention, as hereinabove described, may be formulated for administration by a variety of routes of administration. For example, the antineoplastic product may be formulated in a way that is suitable for topical administration; administration in the eye or the ear; rectal or vaginal administration; as nose drops; by inhalation; as an injectable; or for oral administration. In a preferred embodiment, the antineoplastic product is formulated in a manner such that it is suitable for oral administration.

For example, in formulating the antineoplastic product for topical administration, such as by application to the skin, the at least two different dosage forms, each of which contains an antineoplastic, may be formulated for topical administration by including such dosage forms in an oil-in-water emulsion, or a water-in-oil emulsion. In such a formulation, the immediate release dosage form is in the continuous phase, and the delayed release dosage form is in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

It is also within the scope of the invention to provide an antineoplastic product in the form of a patch, which includes antineoplastic dosage forms having different release profiles, as hereinabove described.

In addition, the antineoplastic product may be formulated for use in the eye or ear or nose, for example, as a liquid emulsion. For example, the dosage form may be coated with a hydrophobic polymer whereby a dosage form is in the oil phase of the emulsion, and a dosage form may be coated with hydrophilic polymer, whereby a dosage form is in the water phase of the emulsion.

Furthermore, the antineoplastic product with at least three different dosage forms with different release profiles may be formulated for rectal or vaginal administration, as known in the art. This may take the form of a cream or emulsion, or other dissolvable dosage form similar to those used for topical administration.

As a further embodiment, the antineoplastic product may be formulated for use in inhalation therapy by coating the particles and micronizing the particles for inhalation.

In a preferred embodiment, the antineoplastic product is formulated in a manner suitable for oral administration.

Thus, for example, for oral administration, each of the dosage forms may be used as a pellet or a particle, with a pellet or particle then being formed into a unitary pharmaceutical product, for example, in a capsule, or embedded in a tablet, or suspended in a liquid for oral administration.

Alternatively, in formulating an oral delivery system, each of the dosage forms of the product may be formulated as a tablet, with each of the tablets being put into a capsule to produce a unitary antineoplastic product. Thus, for example, antineoplastic products may include a first dosage form in the form of a tablet that is an immediate release tablet, and may also include two or more additional tablets, each of which provides for a delayed release of the antineoplastic, as hereinabove described, whereby the $C_{max}$ of the antineoplastic released from each of the tablets is reached at different times, with the $C_{max}$ of the total antineoplastic released from the antineoplastic product being achieved in less than twelve hours.

The formulation of an antineoplastic product including at least three dosage forms with different release profiles for different routes of administration is deemed to be within the skill of the art from the teachings herein. As known in the art, with respect to delayed release, the time of release can be controlled by the concentration of antineoplastics in the coating and/or the thickness of the coating.

In formulating an antineoplastic product in accordance with the invention, in one embodiment, the immediate release dosage form of the product generally provides from about 20% to about 50% of the total dosage of antineoplastic to be delivered by the product, with such immediate release dosage forms generally providing at least 25% of the total dosage of the antineoplastic to be delivered by the product. In many cases, the immediate release dosage form provides from about 20% to about 30% of the total dosage of antineoplastic to be delivered by the product; however, in some cases it may be desirable to have the immediate release dosage form provide for about 45% to about 50% of the total dosage of antineoplastic to be delivered by the product.

The remaining dosage forms deliver the remainder of the antineoplastic. If more than one delayed release dosage form is used, in one embodiment, each of the delayed release dosage forms may provide about equal amounts of antineoplastic; however, they may also be formulated so as to provide different amounts.

In accordance with the present invention, each of the dosage forms contains the same antineoplastic; however, each of the dosage forms may contain more than one antineoplastic.

In one embodiment, where the composition contains one immediate release component and two delayed release components, the immediate release component provides from 20% to 35% (preferably 20% to 30%), by weight, of the total antineoplastic; where there is three delayed release components, the immediate release component provides from 15% to 30%, by weight, of the total antineoplastic; and where there are four delayed release components, the immediate release component provides from 10% to 25%, by weight, of the total antineoplastic.

With respect to the delayed release components, where there are two delayed release components, the first delayed release component (the one released earlier in time) provides from 30% to 60%, by weight, of the total antineoplastic provided by the two delayed release components with the second delayed release component providing the remainder of the antineoplastic.

Where there are three delayed release components, the earliest released component provides 20% to 35% by weight of the total antineoplastic provided by the three delayed release components, the next in time delayed release component provides from 20% to 40%, by weight, of the antineoplastic provided by the three delayed release components and the last in time providing the remainder of the antineoplastic provided by the three delayed release components.

When there are four delayed release components, the earliest delayed release component provides from 15% to 30%, by weight, the next in time delayed release component provides from 15% to 30%, the next in time delayed release component provides from 20% to 35%, by weight, and the last in time delayed release component provides from 20% to 35%, by weight, in each case of the total antineoplastic provided by the four delayed release components.

The Immediate Release Component

The immediate release portion of this system can be a mixture of ingredients that breaks down quickly after administration to release the antineoplastic. This can take the form of either a discrete pellet or granule that is mixed in with, or compressed with, the other three components.

The materials to be added to the antineoplastics for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000–10000) and high molecular weight PEGs (Polyox) with molecular weights above 20,000 daltons.

It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

These materials may be present in the rate of 0.05–15% (W/W).

The Non-pH Sensitive Delayed Release Component

The components in this composition are the same immediate release unit, but with additional polymers integrated into the composition, or as coatings over the pellet or granule.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5–25% (W/W) of this component.

The pH Sensitive (Enteric) Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, and other pthalate salts of cellulose derivatives.

These materials can be present in concentrations from 4–20% (W/W).

Sustained Release Component

The components in this composition are the same as the immediate release component, but with additional polymers integrated into the composition, or as coatings over the pellet or granule.

The kind of materials useful for this purpose can be, but are not limited to, ethylcellulose, hydroxypropylmethylcellulose, hydroxypropylcellulose, hydroxyethylcellulose, carboxymethylcellulose, methylcellulose, nitrocellulose, Eudragit R, and Eudragit RL, Carbopol, or polyethylene glycols with molecular weights in excess of 8,000 daltons.

These materials can be present in concentrations from 4–20% (W/W).

As hereinabove indicated, the units comprising the antineoplastic composition of the present invention can be in the form of discrete pellets or particles contained in the capsule, or particles embedded in a tablet or suspended in a liquid suspension.

The antineoplastic composition of the present invention may be administered, for example, by any of the following routes of administration: sublingual, transmucosal, transdermal, parenteral, etc., and preferably is administered orally. The composition includes a therapeutically effective amount of the antineoplastic, which amount will vary with the antineoplastic to be used, the cancer to be treated, and the number of times that the composition is to be delivered in a day. The composition is administered to a host in an amount effective for treating cancer.

The following are representative examples of agents for the treatment of cancer that may be used in accordance with the invention: carboplatin, busulfan, cisplatin, thiotepa, melphalan hydrochloride, cyclophosphamide, ifosfamide, chlorambucil, mechlorethamine hydrochloride, carmustine, lomustine, streptozocin, polifeprosan 20, dexrazoxane, dronabinol, granisetron hydrochloride, fluconazole, erythropoietin, octreotide acetate, pilocarpine hydrochloride, etidronate disodium, pamidronate disodium, allopurinol sodium, amifostine, filgrastim, mesna, ondansetron hydrochloride, dolasetron mesylate, leucovorin calcium, sargramostim, levamisole hydrochloride, doxorubicin hydrochloride, idarubicin hydrochloride, mitomycin, daunorubicin citrate, plicamycin, daunorubicin hydrochloride, bleomycin sulfate, mitoxantrone hydrochloride, valrubicin, dactinomycin, fludarabine phosphate, cytarabine, mercaptopurine, thioguanine, methotrexate sodium, cladribine, floxuridine, capecitabine, anastrozole, bicalutamide, tamoxifen citrate, testolactone, nilutamide, methyltestosterone, flutamide, toremifene citrate, goserelin acetate, estramustine phosphate sodium, ethinyl estradiol, esterified estrogen, leuprolide acetate, conjugated estrogens, megestrol acetate, aldesleukin, medroxyprogesterone acetate, dacarbazine, hydroxyurea, etoposide phosphate, megestrol acetate, paclitaxel, etoposide, teniposide, trastuzumab, rituximab, vinorelbine tartrate, denileukin diftitox, gemcitabine hydrochloride, vincristine sulfate, vinblastine sulfate, asparaginase, edrophonium chloride, bacillus calmette and guerin, irinotecan hydrochloride, pegaspargase, docetaxel, interferon alfa-2a, recombinant, tretinoin, porfimer sodium, interferon alfa-2b, recombinant, procarbazine hydrochloride, topotecan hydrochloride, altretamine, fluorouracil, prednisolone sodium phosphate, cortisone acetate, dexamethasone, dexamethasone sodium sulfate, dexamethasone acetate, hydrocortisone sodium phosphate, hydrocortisone, prednisolone, methylprednisolone sodium succinate, betamethasone sodium phosphate, betamethasone acetate, letrozole, mithramycin, mitotane, pentostatin, perfosfamide, raloxifene The invention will be further described with respect to the following examples; however, the scope of the invention is not limited thereby. All percentages in this specification, unless otherwise specified, are by weight.

Immediate Release Component

Formulate the composition by mixing the ingredients in a suitable pharmaceutical mixer or granulator such as a planetary mixer, high-shear granulator, fluid bed granulator, or extruder, in the presence of water or other solvent, or in a dry blend. If water or other solvent was used, dry the blend in a suitable pharmaceutical drier, such as a vacuum oven or forced-air oven. The product may be sieved or granulated, and compressed using a suitable tablet press, such as a rotary tablet press.

| Example 1: | | |
|---|---|---|
| | Fluorouracil | 65% (W/W) |
| | Microcrystalline cellulose | 20 |
| | Povidone | 10 |
| | Croscarmellose sodium | 5 |
| Example 2: | | |
| | Fluorouracil | 55% (W/W) |
| | Microcrystalline cellulose | 25 |
| | Povidone | 10 |
| | Croscarmellose sodium | 10 |
| Example 3: | | |
| | Fluorouracil | 65% (W/W) |
| | Microcrystalline cellulose | 20 |
| | Hydroxypropylcellulose | 10 |
| | Croscarmellose sodium | 5 |
| Example 4: | | |
| | Fluorouracil | 75% (W/W) |
| | Polyethylene glycol 4000 | 10 |
| | Polyethylene glycol 2000 | 10 |
| | Hydroxypropylcellulose | 5 |
| Example 5: | | |
| | Fluorouracil | 75% (W/W) |
| | Polyethylene glycol 8000 | 20 |
| | Polyvinylpyrrolidone | 5 |
| Example 6: | | |
| | Dexamethasone | 65% (W/W) |
| | Microcrystalline cellulose | 20 |
| | Hydroxypropylcellulose | 10 |
| | Croscarmellose sodium | 5 |
| Example 7: | | |
| | Dexamethasone | 75% (W/W) |
| | Microcrystalline cellulose | 15 |
| | Hydroxypropylcellulose | 5 |
| | Croscarmellose sodium | 5 |
| Example 8: | | |
| | Dexamethasone | 75% (W/W) |
| | Polyethylene glycol 4000 | 10 |
| | Polyethylene glycol 2000 | 10 |
| | Hydroxypropylcellulose | 5 |
| Example 9: | | |
| | Dexamethasone | 75% (W/W) |
| | Polyethylene glycol 8000 | 20 |
| | Polyvinylpyrrolidone | 5 |
| Example 10: | | |
| | Valrubicin | 65% (W/W) |
| | Microcrystalline cellulose | 20 |
| | Hydroxypropylcellulose | 10 |
| | Croscarmellose sodium | 5 |
| Example 11: | | |
| | Valrubicin | 75% (W/W) |
| | Microcrystalline cellulose | 15 |
| | Hydroxypropylcellulose | 5 |
| | Croscarmellose sodium | 5 |
| Example 12: | | |
| | Valrubicin | 75% (W/W) |
| | Polyethylene glycol 4000 | 10 |
| | Polytheylene glycol 2000 | 10 |
| | Hydroxypropylcellulose | 5 |
| Example 13: | | |
| | Ciprofloxacin | 75% (W/W) |
| | Polyethylene glycol 8000 | 20 |
| | Polyvinylpyrrolidone | 5 |
| Example 14: | | |
| | Tretinoin | 75% (W/W) |
| | Polyethylene glycol 4000 | 10 |
| | Polyethylene glycol 2000 | 10 |
| | Hydroxypropylcellulose | 5 |
| Example 15: | | |
| | Tretinoin | 75% (W/W) |
| | Polyethylene Glycol 4000 | 20 |
| | Polyvinylpyrrolidone | 5 |

Non pH Sensitive Delayed Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool, the product may be sieved or granulated, and compressed using a suitable tablet press, such as a rotary tablet press.

| | Ingredient | Conc. (% W/W) |
|---|---|---|
| Example 16: | | |
| | Fluorouracil | 65% (W/W) |
| | Microcrystalline cellulose | 20 |
| | Polyox | 10 |
| | Croscarmellose sodium | 5 |
| Example 17: | | |
| | Fluorouracil | 55% (W/W) |
| | Microcrystalline cellulose | 25 |
| | Polyox | 10 |
| | Glyceryl monooleate | 10 |
| Example 18: | | |
| | Fluorouracil | 65% (W/W) |
| | Polyox | 20 |
| | Hydroxypropylcellulose | 10 |
| | Croscarmellose sodium | 5 |

| Ingredient | Conc. (% W/W) |
|---|---|
| Example 19: | |
| Dexamethasone | 70% (W/W) |
| Polyox | 20 |
| Hydroxypropylcellulose | 5 |
| Croscarmellose sodium | 5 |

Enteric Release Component

Formulate the ingredients by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool, the product may be sieved or granulated, and compressed using a suitable tablet press, such as a rotary tablet press.

| Ingredient | Conc. (% W/W) |
|---|---|
| Example 20: | |
| Fluorouracil | 65% (W/W) |
| Microcrystalline cellulose | 20 |
| Cellulose Acetate Pthalate | 15 |
| Example 21: | |
| Fluorouracil | 55% (W/W) |
| Microcrystalline cellulose | 25 |
| Cellulose Acetate Pthalate | 10 |
| Hydroxypropylmethylcellulose | 10 |
| Example 22: | |
| Fluorouracil | 65% (W/W) |
| Polyox | 20 |
| Hydroxypropylcellulose pthalate | 10 |
| Eudragit L30D | 5 |
| Example 23: | |
| Fluorouracil | 40% (W/W) |
| Microcrystalline Cellulose | 40 |
| Cellulose Acetate Pthalate | 10 |
| Example 24: | |
| Dexamethasone | 70% (W/W) |
| Hydroxypropylcellulose pthalate | 15 |
| Croscarmellose sodium | 10 |
| Example 25: | |
| Dexamethasone | 75% (W/W) |
| Polyethylene glycol 2000 | 10 |
| Eudragit L 30D | 15 |
| Example 26: | |
| Dexamethasone | 40% (W/W) |
| Lactose | 50 |
| Eudragit L 30D | 10 |
| Example 27: | |
| Valrubicin | 65% (W/W) |
| Microcrystalline Cellulose | 20 |
| Eudragit L 30D | 10 |
| Example 28: | |
| Valrubicin | 75% (W/W) |
| Microcrystalline Cellulose | 15 |
| Hydroxypropylcellulose pthalate | 10 |

| Ingredient | Conc. (% W/W) |
|---|---|
| Example 29: | |
| Valrubicin | 80% (W/W) |
| Lactose | 10 |
| Eudragit L 30D | 10 |
| Example 30: | |
| Valrubicin | 70% (W/W) |
| Polyethylene glycol 4000 | 20 |
| Cellulose acetate pthalate | 10 |
| Example 31: | |
| Tretinoin | 60% (W/W) |
| Polyethylene glycol 2000 | 10 |
| Lactose | 20 |
| Eudragit L 30D | 10 |
| Example 32: | |
| Tretinoin | 70% (W/W) |
| Microcrystalline cellulose | 20 |
| Cellulose acetate pthalate | 10 |

Sustained Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool, the product may be sieved or granulated, and compressed using a suitable tablet press, such as a rotary tablet press.

| Ingredient | Conc. (% W/W) |
|---|---|
| Example 33: | |
| Fluorouracil | 65% (W/W) |
| Ethylcellulose | 20 |
| Polyox | 10 |
| Hydroxypropylmethylcellulose | 5 |
| Example 34: | |
| Fluorouracil | 55% (W/W) |
| Lactose | 25 |
| Polyox | 10 |
| Glyceryl monooleate | 10 |
| Example 35: | |
| Fluorouracil | 70% (W/W) |
| Polyox | 20 |
| Hydroxypropylcellulose | 10 |
| Example 36: | |
| Dexamethasone | 75% (W/W) |
| Lactose | 15 |
| Hydroxypropylcellulose | 5 |
| Ethylcellulose | 5 |
| Example 37: | |
| Dexamethasone | 75% (W/W) |
| Polyethylene glycol 4000 | 10 |
| Lactose | 10 |
| Eudragit RL 30D | 5 |
| Example 38: | |
| Dexamethasone | 80% (W/W) |
| Polyethylene glycol 8000 | 10 |
| Hydroxypropylmethylcellulose | 5 |
| Eudragit RS 30D | 5 |

-continued

| Ingredient | Conc. (% W/W) |
|---|---|
| Example 39: | |
| Valrubicin | 75% (W/W) |
| Hydroxyethylcellulose | 10 |
| Polyethylene glycol 4000 | 10 |
| Hydroxypropylcellulose | 5 |
| Example 40: | |
| Valrubicin | 75% (W/W) |
| Lactose | 10 |
| Povidone (PVP) | 10 |
| Polyethylene glycol 2000 | 5 |
| Example 41: | |
| Tretinoin | 75% (W/W) |
| Polyethylene glycol 4000 | 10 |
| Povidone (PVP) | 10 |
| Hydroxypropylcellulose | 5 |
| Example 42: | |
| Tretinoin | 75% (W/W) |
| Lactose | 15 |
| Polyethylene glycol 4000 | 5 |
| Polyvinylpyrrolidone | 5 |
| Example 43: | |
| Dexamethasone | 40% (W/W) |
| Eudragit S100 | 50 |
| Triethyl Citrate | 10 |
| Example 44: | |
| Dexamethasone | 50% (W/W) |
| Sureteric | 50 |
| Example 45: | |
| Dexamethasone | 50% (W/W) |
| Eudragit S100 | 45 |
| Triethyl Citrate | 5 |

Three Pulses

EXAMPLE 46

Antineoplastic Agent Matrix Pellet Formulation and Preparation Procedure
(Immediate Release)

46.1. Pellet Formulation

The composition of the antineoplastic agent matrix pellets provided in Table 1.

TABLE 1

Composition of Antineoplastic Pellets

| Component | Percentage (%) |
|---|---|
| Antineoplastic agent | 50 |
| Avicel PH 101 | 20 |
| Lactose | 20 |
| PVP K29/32* | 10 |
| Purified Water | |
| Total | 100 |

*PVP K29/32 was added as a 20% w/w aqueous solution during wet massing.

46.2 Preparation Procedure for Antineoplastic Agent Matrix Pellets 46.2.1 Blend antineoplastic agent and Avicel® PH 101 using a Robot Coupe high shear granulator.

46.2.2 Add 20% Povidone K29/32 binder solution slowly into the powder blend under continuous mixing.

46.2.3 Extrude the wet mass using an LCI Bench Top Granulator. The diameter of the screen of the Bench Top Granulator was 1.0 mm.

46.2.4 Spheronize the extrudate using a Model SPH20 Caleva Spheronizer.

46.2.5 Dry the spheronized pellets at 50° C. overnight.

46.2.6 Pellets between 16 and 30 Mesh were collected for further processing.

46.3 Preparation of an Eudragit® L 30 D-55 Aqueous Coating Dispersion

A. Dispersion Formulation

The composition of the aqueous Eudragit L30D-55 dispersion applied to the antineoplastic agent matrix pellets is provided below in Table 2.

TABLE 2

Eudragit ® L 30 D-55 Aqueous Coating Dispersion

| Component | Percentage (%) |
|---|---|
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

B. Preparation Procedure for an Eudragit® L 30 D-55 Aqueous Dispersion 46.3.1 Suspend triethyl citrate and talc in deionized water.

46.3.2 The TEC/talc suspension is then homogenized using a PowerGen 700 high shear mixer.

46.3.3 Add the TEC/talc suspension slowly to the Eudragit® L 30 D-55 latex dispersion while stirring.

46.3.4 Allow the coating dispersion to stir for one hour prior to application onto the antineoplastic agent matrix pellets.

46.4 Preparation of an Eudragit® S 100 Aqueous Coating Dispersion

A. Dispersion Formulation

The composition of the aqueous Eudragit® S 100 dispersion applied to the antineoplastic agent matrix pellets is provided below in Table 3.

TABLE 3

Eudragit ® S 100 Aqueous Coating Dispersion

| Component | Percentage (%) |
|---|---|
| Part A | |
| Eudragit ® S 100 | 12.0 |
| 1 N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

B. Preparation Procedure for an Eudragit® S 100 Aqueous Dispersion

Part I:

(i) Dispense Eudragit® S 100 powder in deionized water with stirring.

(ii) Add ammonium hydroxide solution drop-wise into the dispersion with stirring.
(iii) Allow the partially neutralized dispersion to stir for 60 minutes.
(iv) Add triethyl citrate drop-wise into the dispersion with stirring. Stir for about 2 hours prior to the addition of Part B.

Part II:
(i) Disperse talc in the required amount of water
(ii) Homogenize the dispersion using a PowerGen 700D high shear mixer.
(iii) Part B is then added slowly to the polymer dispersion in Part A with a mild stirring.

46.5 Coating Conditions for the Application of Aqueous Coating Dispersions

The following coating parameters are used to coat matrix pellets with each of the Eudragit® L 30 D-55 and Eudragit® S 100 aqueous film coating.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

(i) Coat matrix pellets with L30 D-55 dispersion such that you apply 12% coat weight gain to the pellets.
(ii) Coat matrix pellets with S100 dispersion such that you apply 20% coat weight gain to the pellets.

46.6 Encapsulation of the Antineoplastic Agent Pellets

Pellets are filled into size 00 hard gelatin capsules at a ratio of 30%:30%:40%:Immediate-release matrix pellets uncoated, L30 D-55 coated pellets and S100 coated pellets respectively. The capsule is filled with the three different pellets to achieve the desired dosage.

Three Pulses

EXAMPLE 47

Antineoplastic Agent Pellet Formulation and Preparation Procedure 47.1 Pellet Formulations for Subsequent Coating The composition of the Antineoplastic agent trihydrate matrix pellets provided in Table 4.

TABLE 4

Composition of Antineoplastic agent Matrix Pellets

| Component | Percentage (%) |
|---|---|
| Antineoplastic agent Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

47.2 Preparation Procedure for Antineoplastic Agent Matrix Pellets
47.2.1 Blend Antineoplastic agent and Avicel® PH 101 using a low shear blender.
47.2.2 Add the hydroxypropyl methylcellulose binder solution slowly into the powder blend under continuous mixing.
47.2.3 Extrude the wet mass using an LCI Bench Top Granulator. The diameter of the screen of the Bench Top Granulator is 0.8 mm.
47.2.4 Spheronize the extrudate using a QJ-230 Spheronizer using a small cross section plate.
47.2.5 Dry the spheronized pellets at 60° C. using a fluid bed dryer until the exhaust temperature reaches 40° C.
47.2.6 Pellets between 20 and 40 Mesh were collected for further processing.

47.3 Preparation of an Eudragit® L 30 D-55 Aqueous Coating Dispersion
47.3.1 Dispersion Formulation The composition of the aqueous Eudragit L30D-55 dispersion applied to the antineoplastic agent matrix pellets is provided below in Table 5.

TABLE 5

Eudragit ® L 30 D-55 Aqueous Coating Dispersion

| Component | Percentage (%) |
|---|---|
| Eudragit ® L 30 D-55 | 41.6 |
| Triethyl Citrate | 2.5 |
| Talc | 5.0 |
| Purified Water | 50.9 |
| Solids Content | 20.0 |
| Polymer Content | 12.5 |

47.4 Preparation Procedure for an Eudragit® L 30 D-55 Aqueous Dispersion
47.4.1 Suspend triethyl citrate and talc in deionized water.
47.4.2 The TEC/talc suspension is mixed using laboratory mixer.
47.4.3 Add the TEC/talc suspension from slowly to the Eudragit® L 30 D-55 latex dispersion while stirring.
47.4.4 Allow the coating dispersion to stir for one hour prior to application onto the antineoplastic agent matrix pellets.

47.5 Preparation of an Eudragit® S 100 Aqueous Coating Dispersion
47.5.1 Dispersion Formulation The composition of the aqueous Eudragit® S 100 dispersion applied to the Antineoplastic agent matrix pellets is provided below in Table 6.

TABLE 6

Eudragit ® S 100 Aqueous Coating Dispersion

| Component | Percentage (%) |
|---|---|
| Part A | |
| Eudragit ® S 100 | 10.0 |
| 1 N Ammonium Hydroxide | 5.1 |
| Triethyl Citrate | 5.0 |
| Water | 64.9 |
| Part B | |
| Talc | 5.0 |
| Water | 10.0 |
| Solid Content | 25.0 |
| Polymer Content | 10.0 |

47.6 Preparation Procedure for an Eudragit® S 100 Aqueous Dispersion

Part A:

47.6.1 Dispense Eudragit® S 100 powder in deionized water with stirring.

47.6.2 Add ammonium hydroxide solution drop-wise into the dispersion with stirring.

47.6.3 Allow the partially neutralized dispersion to stir for 60 minutes.

47.6.4 Add triethyl citrate drop-wise into the dispersion with stirring and let stir overnight prior to the addition of Part B.

Part B:

47.6.5 Disperse talc in the required amount of water 47.6.6 Stir the dispersion using an overhead laboratory mixer.

47.6.7 Part B is then added slowly to the polymer dispersion in Part A with a mild stirring.

47.7 Coating Conditions for the Application of Aqueous Coating Dispersions

The following coating parameters are used for both the Eudragit® L 30 D-55 and Eudragit® S 100 aqueous film coating processes.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2–6 gram per minute |

47.7.1 Coat matrix pellets with L30 D-55 dispersion such that you apply 20% coat weight gain to the pellets.

47.7.2 Coat matrix pellets with S100 dispersion such that you apply 37% coat weight gain to the pellets.

47.8 Preparation of Antineoplastic Agent Granulation (Immediate Release Component) for Tabletting

TABLE 7

Composition of Antineoplastic agent Granulation

| Component | Percentage (%) |
|---|---|
| Antineoplastic agent Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

47.8.2 Blend Antineoplastic agent and Avicel® PH 101 using a low shear blender.

47.8.3 Add the hydroxypropyl methylcellulose binder solution slowly into the powder blend under continuous mixing.

47.8.4 Dry the granulation at 60° C. using a fluid bed dryer until the exhaust temperature reaches 40° C.

47.8.5 Granules between 20 and 40 Mesh are collected for further processing.

47.9 Tabletting of the Antineoplastic Agent Pellets

TABLE 8

Composition of Antineoplastic agent Tablets

| Component | Percentage (%) |
|---|---|
| Antineoplastic agent granules | 32.5 |
| Avicel PH 200 | 5.0 |
| Antineoplastic agent L30D-55 coated pellets | 30 |
| Antineoplastic agent S100 coated pellets | 30 |
| Colloidal silicon dioxide | 1.5 |
| Magnesium stearate | 1.0 |
| Total | 100 |

47.9.1 Blend the Antineoplastic agent granules, Avicel PH-200, Antineoplastic agent pellets and colloidal silicon dioxide for 15 minutes in a tumble blender.

47.9.2 Add the magnesium stearate to the blender, and blend for 5 minutes.

47.9.3 Compress the blend on a rotary tablet press.

47.9.4 The fill weight should be adjusted to achieve the desired dosage.

Four Pulses

EXAMPLE 48

1 Antineoplastic Matrix Pellet Formulation and Preparation Procedure 48.1 Pellet Formulation The composition of the antineoplastic agent matrix pellets is provided in Table 9.

TABLE 9

Composition of Antineoplastic agent Pellets

| Component | Percentage (%) |
|---|---|
| Antineoplastic agent | 50 |
| Avicel PH 101 | 20 |
| Lactose | 20 |
| PVP K29/32* | 10 |
| Purified Water | |
| Total | 100 |

*PVP K29/32 was added as a 20% w/w aqueous solution during wet massing.

48.2 Preparation Procedure for Antineoplastic Agent Matrix Pellets 48.2.1 Blend antineoplastic agent and Avicel® PH 101 using a Robot Coupe high shear granulator.

48.2.2 Add 20% Povidone K29/32 binder solution slowly into the powder blend under continuous mixing.

48.2.3 Extrude the wet mass using an LCI Bench Top Granulator. The diameter of the screen of the Bench Top Granulator was 1.0 mm.

48.2.4 Spheronize the extrudate using a Model SPH20 Caleva Spheronizer.

48.2.5 Dry the spheronized pellets at 50° C. overnight.

48.2.6 Pellets between 16 and 30 Mesh were collected for further processing.

48.3 Preparation of an Eudragit® L 30 D-55 Aqueous Coating Dispersion 48.3.1 Dispersion Formulation The composition of the aqueous Eudragit L30D-55 dispersion applied to the antineoplastic agent matrix pellets is provided below in Table 10.

TABLE 10

Eudragit ® L 30 D-55 Aqueous Coating Dispersion

| Component | Percentage (%) |
|---|---|
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

48.4 Preparation Procedure for an Eudragit® L 30 D-55 Aqueous Dispersion
48.4.1 Suspend triethyl citrate and talc in deionized water.
48.4.2 The TEC/talc suspension is then homogenized using a PowerGen 700 high shear mixer.
48.4.3 Add the TEC/talc suspension slowly to the Eudragit® L 30 D-55 latex dispersion while stirring.
48.4.4 Allow the coating dispersion to stir for one hour prior to application onto the antineoplastic agent matrix pellets.

48.5 Preparation of an Eudragit® S 100 Aqueous Coating Dispersion
48.5.1 Dispersion Formulation The composition of the aqueous Eudragit® S 100 dispersion applied to the antineoplastic agent matrix pellets is provided below in Table 11.

TABLE 11

Eudragit ® S 100 Aqueous Coating Dispersion

| Component | Percentage (%) |
|---|---|
| Part A | |
| Eudragit ® S 100 | 12.0 |
| 1 N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

48.6 Preparation Procedure for an Eudragit® S 100 Aqueous Dispersion
Part A:
48.6.1 Dispense Eudragit® S 100 powder in deionized water with stirring.
48.6.2 Add ammonium hydroxide solution drop-wise into the dispersion with stirring.
48.6.3 Allow the partially neutralized dispersion to stir for 60 minutes.
48.6.4 Add triethyl citrate drop-wise into the dispersion with stirring. Stir for about 2 hours prior to the addition of Part B.
Part B:
48.6.5 Disperse talc in the required amount of water
48.6.6 Homogenize the dispersion using a PowerGen 700D high shear mixer.
48.6.7 Part B is then added slowly to the polymer dispersion in Part A with a mild stirring.

48.7 Coating Conditions for the Application of Aqueous Coating Dispersions

The following coating parameters are used for coating with each of the Eudragit® L 30 D-55 and Eudragit® S 100 aqueous film coatings.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

48.7.1 Coat matrix pellets with L30 D-55 dispersion such that you apply 12% coat weight gain to the pellets.
48.7.2 Coat matrix pellets with L30 D-55 dispersion such that you apply 30% coat weight gain to the pellets.
48.7.3 Coat matrix pellets with S 100 dispersion such that you apply 20% coat weight gain to the pellets.

48.8 Encapsulation of the Antineoplastic agent Pellets

Pellets are filled into size 00 hard gelatin capsules at a ratio of 20%:30%:20%:30% Immediate-release matrix pellets (uncoated), L30 D-55 coated pellets 12% weight gain, L30D-55 coated pellets 30% weight gain and S100 coated pellets respectively. The capsule is filled with the four different pellets to achieve the desired dosage.

The present invention is particularly advantageous in that there is provided an antineoplastic product which provides an improvement over twice a day administration of the antineoplastic and an improvement over a once a day administration of such agent.

Numerous modification and variations of the present invention are possible in light of the above teachings and therefore, within the scope of the appended claims the invention may be practiced otherwise than as particularly described.

The invention claimed is:

1. A once-a-day antineoplastic product comprising: first, second, and third dosage forms, wherein each of said dosage forms includes at least one antineoplastic agent and a pharmaceutically acceptable carrier; said first dosage form is an immediate release dosage form; said second and third dosage forms are delayed release dosage forms; each of said first, second, and third dosage forms initiates release of said at least one antineoplastic agent at different times; Cmax in serum of the total antineoplastic agent released from said antineoplastic product is achieved in less than about 12 hours from administration; and said once-a-day antineoplastic product contains the total dosage of said at least one antineoplastic agent for a twenty-four hour period.

2. The product of claim 1, wherein the Cmax for the product is reached no earlier than four hours after administration.

3. The product of claim 1, wherein the antineoplastic released from the first dosage form reaches a Cmax within from about 0.5 hours to about 2 hours after administration of the product.

4. The product of claim 1, wherein the antineoplastic released from the second dosage form reaches a Cmax in no more than about 4 hours after administration of the product.

5. The product of claim 1, wherein the antineoplastic released from the third dosage form reaches a Cmax within 8 hours after administration of the product.

6. The product of claim 1, wherein the immediate release dosage form contains at least 20% and no more than 50% of the total dosage of antineoplastic.

7. The product of claim 1, wherein the product is an oral dosage form.

8. The product of claim 1, wherein the antineoplastic released from the second dosage form reaches a Cmax after Cmax is reached for the antineoplastic released from the first dosage form.

9. The product of claim 1, wherein the antineoplastic released from the third dosage form reaches a Cmax after Cmax is reached for the antineoplastic released from the second dosage form.

10. The product of claim 1 further comprising a fourth antineoplastic dosage form, said fourth antineoplastic dosage form being a delayed release dosage form and comprising at least one antineoplastic and a pharmaceutically acceptable carrier and wherein said at least one antineoplastic released from said fourth antineoplastic dosage form reaches a Cmax after Cmax is achieved for antineoplastic released from each of said first, second, and third dosage forms.

11. The product of claim 10, wherein the Cmax for the product is reached no earlier than four hours after administration.

12. The product of claim 10, wherein the antineoplastic released from the first dosage form reaches a Cmax within from about 0.5 hours to about 2 hours after administration of the product.

13. The product of claim 10, wherein the antineoplastic released from the second dosage form reaches a Cmax in no more than about 4 hours after administration of the product.

14. The product of claim 10, wherein the antineoplastic released from the third dosage form reaches a Cmax within 8 hours after administration of the product.

15. The product of claim 10, wherein said second dosage form initiates release of said antineoplastic before said third dosage form, wherein said third dosage form initiates release of said antineoplastic before said fourth dosage form, wherein said second dosage form provides 20% to 35% by weight of the total antineoplastic released by said second, third, and fourth dosage forms, wherein said third dosage form provides from 20% to 40% by weight of the total antineoplastic released by said second, third, and fourth dosage forms, and wherein said fourth dosage form provides the remainder of the total antineoplastic released by said second, third, and fourth dosage forms.

16. The product of claim 10, wherein the product is an oral dosage form.

17. The product of claim 10, wherein the antineoplastic released from the second dosage form reaches a Cmax after Cmax is reached for the antineoplastic released from the first dosage form.

18. The product of claim 10, wherein the antineoplastic released from the third dosage form reaches a Cmax after Cmax is reached for the antineoplastic released from the second dosage form.

19. The once-a-day antineoplastic product of claim 1, wherein said at least one antineoplastic agent is in the form of a salt.

20. The once-a-day antineoplastic product of claim 10, wherein said at least one antineoplastic agent is in the form of a salt.

21. A process for treating cancer in a host comprising: administering to a host the antineoplastic product of claim 1, once-a-day.

22. A process for treating cancer in a host comprising: administering to a host the antineoplastic product of claim 2, once-a-day.

23. A process for treating cancer in a host comprising: administering to a host the antineoplastic product of claim 3, once-a-day.

24. A process for treating cancer in a host comprising: administering to a host the antineoplastic product of claim 4, once-a-day.

25. A process for treating cancer in a host comprising: administering to a host the antineoplastic product of claim 5, once-a-day.

26. A process for treating cancer in a host comprising: administering to a host the antineoplastic product of claim 6, once-a-day.

27. A process for treating cancer in a host comprising: administering to a host the antineoplastic product of claim 7, once-a-day.

28. A process for treating cancer in a host comprising: administering to a host the antineoplastic product of claim 8, once-a-day.

29. A process for treating cancer in a host comprising: administering to a host the antineoplastic product of claim 9, once-a-day.

30. A process for treating cancer in a host comprising: administering to a host the antineoplastic product of claim 10, once-a-day.

31. A process for treating cancer in a host comprising: administering to a host the antineoplastic product of claim 11, once-a-day.

32. A process for treating cancer in a host comprising: administering to a host the antineoplastic product of claim 12, once-a-day.

33. A process for treating cancer in a host comprising: administering to a host the antineoplastic product of claim 13, once-a-day.

34. A process for treating cancer in a host comprising: administering to a host the antineoplastic product of claim 14, once-a-day.

35. A process for treating cancer in a host comprising: administering to a host the antineoplastic product of claim 15, once-a-day.

36. A process for treating cancer in a host comprising: administering to a host the antineoplastic product of claim 16, once-a-day.

37. A process for treating cancer in a host comprising: administering to a host the antineoplastic product of claim 17, once-a-day.

38. A process for treating cancer in a host comprising: administering to a host the antineoplastic product of claim 18, once-a-day.

39. A process for treating cancer in a host comprising: administering to a host the antineoplastic product of claim 19, once-a-day.

40. A process for treating cancer in a host comprising: administering to a host the antineoplastic product of claim 20, once-a-day.

41. A process for treating a patient with an antineoplastic agent said process for treating comprising:
    administering to a patient once-a-day an antineoplastic product, said product comprising: first, second, and third dosage forms, wherein each of said dosage forms includes at least one antineoplastic agent and a pharmaceutically acceptable carrier; said treating including an immediate release of antineoplastic from said first dosage form and delayed releases of antineoplastic from each of said second and third dosage forms, said immediate release and two delayed releases initiating release of antineoplastic at different times to produces a $C_{max}$ in serum of the total antineoplastic agent released from said antineoplastic product in less than about 12 hours from administration; and said treating delivers the total dosage of said at least one antineoplastic agent for a twenty-four hour period.

* * * * *